United States Patent
Schmidt et al.

[11] Patent Number: 5,817,334
[45] Date of Patent: Oct. 6, 1998

[54] METHOD OF MAKING LIPOSOMES WITH IMPROVED STABILITY DURING DRYING

[75] Inventors: Paul G. Schmidt, San Marino; Gary Fujii, Torrance, both of Calif.

[73] Assignee: NeXstar Pharmaceuticals, Inc., Boulder, Colo.

[21] Appl. No.: 469,156

[22] Filed: Jun. 6, 1995

Related U.S. Application Data

[63] Continuation of Ser. No. 534,348, Jun. 5, 1990, abandoned, which is a continuation of Ser. No. 253,680, Oct. 5, 1988, abandoned.

[51] Int. Cl.$^6$ .............................. A61K 9/10; A61K 9/127; B01J 13/02
[52] U.S. Cl. .......................... 424/450; 264/4.3; 436/829
[58] Field of Search .................................... 424/450, 1.21, 424/417, 418; 264/4.1, 4.3; 427/213.3, 213.31; 428/402.2; 436/829; 514/937

[56] References Cited

U.S. PATENT DOCUMENTS

| | | | |
|---|---|---|---|
| 4,016,100 | 4/1977 | Suzuki et al. | 264/4.3 |
| 4,193,983 | 3/1980 | Ullman et al. | 436/528 |
| 4,229,360 | 10/1980 | Schneider et al. | 264/4.6 |
| 4,235,871 | 11/1980 | Papahadjopoulos et al. | 424/450 |
| 4,377,567 | 3/1983 | Geho | 424/1.21 |
| 4,411,894 | 10/1983 | Schrank et al. | 514/221 |
| 4,460,560 | 7/1984 | Jokes et al. | 424/1.37 |
| 4,544,545 | 10/1985 | Ryan et al. | 424/1.21 |
| 4,568,545 | 2/1986 | Mihara et al. | 424/94.64 |
| 4,735,210 | 4/1988 | Goldonberg | 424/1.29 |
| 4,746,516 | 5/1988 | Moro et al. | 424/450 |
| 4,769,250 | 9/1988 | Forssen | 424/450 |
| 4,857,319 | 8/1989 | Crowe et al. | 424/94.1 |
| 4,880,635 | 11/1989 | Janoff et al. | 424/450 |
| 4,883,665 | 11/1989 | Miyazima et al. | 424/417 |
| 4,914,084 | 4/1990 | Ecanow | 514/6 |
| 5,008,109 | 4/1991 | Tin | 424/1.21 |
| 5,089,181 | 2/1992 | Hauser | 264/4.3 |
| 5,705,187 | 1/1998 | Unger . | |

FOREIGN PATENT DOCUMENTS

| | | |
|---|---|---|
| 57-004913 A | 1/1982 | Japan . |
| 2-273538 | 11/1990 | Japan . |
| 2013609 | 8/1979 | United Kingdom . |
| 8601103 | 2/1986 | WIPO . |
| 8603938 | 7/1986 | WIPO . |
| 8701933 | 4/1987 | WIPO . |
| 8705300 | 9/1987 | WIPO . |

OTHER PUBLICATIONS

Szoka & Paphadojopoulos, Ann. Rev. Biophys. Bioeng. vol. 9, pp. 467–508 (1980).

Lipossome Technology vol. I, Allen pp. 110–112, Rao pp. 249–255 (1984).

Poznansky & Juliano, Pharmacological Reviews vol. 36, pp. 277–336 (1984).

Ryman & Tyrrell, Essays Biochemistry vol. 16, pp. 49–98 (1980).

Gregoriadis, Trends in Biotechnology vol. 3, pp. 235–241 (1985).

Strauss & Hauser, Proc. Natl. Acad. Aci. USA vol. 83, pp. 2422–2426 (1986).

MacKenzie, Develop. Biol. Standard vol. 36, pp. 51–67 (1977).

MacKenize, Bull. Parenteral Drug Assoc. vol. 20, pp. 101–129 (1966).

(List continued on next page.)

Primary Examiner—JoséG. Dees
Assistant Examiner—Robert H. Harrison
Attorney, Agent, or Firm—NeXstar Pharmaceuticals, Inc.

[57] ABSTRACT

A composition and method are provided for the making of cholesterol containing phospholipid liposomes such that when dried and then reconstituted, the liposomes retain their structure and size distribution as well as substantially all of the material that was originally encapsulated, and they behave biologically in a normal fashion. The cryoprotective agents are used in the aqueous medium to hydrate the phospholipid(s) and are a combination of at least one sugar and at least one protein, polypeptide, and/or oligopeptide.

12 Claims, 1 Drawing Sheet

OTHER PUBLICATIONS

Racker, J. Membrane Biol. vol. 10, pp. 221–235 (1972).
Madden et al., Biochim. Biophys, Acta vol. 817, pp. 67–74 (1985).
Crowe et al., Arch. Biochem, Biophys. vol. 242, pp. 240–247 (1985).
Crowe et al., Biophysical Journal vol. 47,248a (1985).
Crommelin & van Bommel, Pharmaceutical Research vol. 3, pp. 159–163 (1984).

Mauk & Gamble, Anal. Biochem. vol. 94, pp. 302–307 (1979).
Crowe et al., Biochem. J. vol. 242, pp. 1–10 (1987).
Tsyganenko et al., Antiobiotiki vol. 28, pp. 577–581 (1983).
Yasui et al., Cryoprotective Effect of Gelatin and Albumin on Recombinant Human Tumor Necrosis Factor Liposome, Chemical & Pharmaceutical Bulletin, 41(12), Dec. 1993, pp. 2138–2140.

METHOD OF MAKING LIPOSOMES WITH IMPROVED STABILITY DURING DRYING

This application is a continuation of U.S. Ser. No. 07/534,348, filed Jun. 5, 1990, now abandoned, which is a continuation of U.S. Ser. No. 07/253,680, filed Oct. 5, 1988, now abandoned.

FIELD OF THE INVENTION

This invention relates generally to making liposomes that are stable during drying which may contain drugs or other therapeutic agents, diagnostic agents, or other materials of biological or pharmacological interest. In the preferred embodiment, the liposomes are made in the presence of the combination of at least one sugar and at least one protein, polypeptide and/or oligopeptide, whereby upon reconstitution of the dried stabilized liposome, the liposome bilayer is maintained, aggregation or fusion is avoided, and the degree of drug encapsulation achievable on reconstitution is greatly improved.

BACKGROUND OF THE INVENTION

Liposomes are described quite widely in the literature and their structure is well known. Liposomes are unilamellar or multilamellar lipid vesicles which enclose a fluid space or spaces. The walls of the liposomes are formed by a bilayer of one or more lipid components having polar heads and non-polar tails. In an aqueous (or polar) solution, the polar heads of one layer orient outwardly to extend into the surrounding medium, and the non-polar tail portions of the lipids associate with each other, thus providing a polar surface and a non-polar core in the wall of the liposome. Unilamellar liposomes have one such bilayer, whereas multilamellar liposomes generally have a plurality of substantially concentric bilayers.

A variety of methods for preparing liposomes are known, many of which have been described by Szoka and Papahadjopoulos, *Ann. Rev. Biophysics Bioeng.* 9: 467–508 (1980) and in *Liposome Technology*, Preparation of Liposomes, Vol I, Gregoriadis (Ed.), CRC Press, Inc. (1984). Also, several liposome encapsulation methods are disclosed in the patent literature, notably in U.S. Pat. No. 4,235,871, issued to Papahadjopoulos et al. on Nov. 25, 1980, and in U.S. Pat. No. 4,016,100, issued to Suzuki et al. on Apr. 5, 1977.

Liposomes are recognized as useful for encapsulation of drugs and other therapeutic agents and for carrying these agents to selected in vivo sites. Drug administration via liposomes can result in reduced toxicity, altered tissue distribution, increased drug effectiveness, and an improved therapeutic index. See generally M. J. Poznansky and R. L. Juliano, *Biological Approaches to the Controlled Delivery of Drugs: A Critical Review* in Pharmacological Review, 36, 296–305 (1984); B. E. Ryman and D. A. Tyrrell, *Liposomes—Bags of Potential* in Biochemistry, 21, 49–98 (1980).

Liposomes have also been used successfully for introducing various chemicals, biochemicals, genetic material and the like into viable cells in vitro, and as carriers for diagnostic agents. See generally M. J. Poznansky and R. L. Juliano, supra; B. E. Ryman and D. A. Tyrrell, supra.

Recently unilamellar liposomes have become important in several research areas dealing with membrane mediated processes such as membrane fusion, interfacial catalysis, energy conduction and conversion, drug delivery and targeting. This kind of research has already led to industrial applications of unilamellar and multilamellar liposomes for drug delivery and diagnostic imaging.

Although encapsulation of therapeutic agents and diagnostic agents in liposomes has significant commercial potential, a major difficulty encountered in the commercial production of liposome encapsulates is the lack of long term stability of the liposome itself and/or the encapsulated agent(s).

Liposomal stability on storage is defined generally as the extent to which a given preparation retains both its original structure, chemical composition, and size distribution and if applicable, its load of incorporated agent, whether therapeutic or diagnostic in nature. Instability can occur, for example, when liposome size increases spontaneously upon standing as a result of fusion of colliding liposomes. Some small unilamellar liposomes (SUV) made of zwitterionic phosphatidylcholines tend to aggregate and/or fuse to large multilamellar lipid particles at room temperature. The larger liposomes will exhibit drastically different pharmacokinetics in vivo because their size determines their clearance rates and tissue distribution; for instance, large liposomes are removed from the circulation more rapidly than smaller ones. In addition, liposomes in an aqueous liposome dispersion can aggregate and precipitate as a sediment. Although such sediments can usually be re-dispersed, the structure and size distribution of the original dispersion may be changed. Finally, another important factor with regard to instability is that incorporated substances of low molecular weight are likely to leak from stored liposomes. See generally G. Gregoriadis, *Liposomes for Drugs and Vaccines* in Trends in Biotechnology, 3, 235–241 (1985). Such leakage can represent a significant proportion of the total content of the agent in the liposomes.

Research directed to prolonging liposomal stability on storage has included liposome preservation in the form of lyophilization. Lyophilization refers to the process whereby a substance is prepared in dry form by freezing and dehydration. A liposome can be lyophilized with or without loaded therapeutics, diagnostics, or other agents of biological interest. If lyophilized without such agents, such agents can be subsequently loaded after reconstitution of the liposomes by methods well known in the art. Drying methods other than lyophilization can be used in the invention, for example, spray, tray, and drum drying as well as that disclosed in co-pending serial No. 018,190 which is incorporated herein by reference.

Breakage of the liposomes during drying is common when cryoprotectants are not used. This causes leakage or release of the encapsulated contents. In addition, the process of fusion and aggregation of unilamellar vesicles is greatly accelerated when they are subjected to freeze-thawing or dehydration. It has been shown that small unilamellar vesicles of egg phosphatidylcholine revert to large multilamellar structures upon freezing and thawing. G. Strauss and H. Hauser, Proc. Natl. Acad. Sci. U.S.A. 83, 2422 (1986), the disclosure of which is incorporated herein by reference.

Cryoprotectants may be used to protect the dehydrated product and keep it in a condition suitable for future use. The dehydrated product can then be reconstituted by the addition of distilled water or appropriate solution. Hydrophilic substances such as dextran, mannitol, lactose, and polyvinylpyrollidone are well known in the art as cryoprotectants for cells and tissue (MacKenzie, A. P. (1976) Develop. biol. Standard 36, 51–67) as well as bulking agents for biologicals and pharmaceuticals that are lyophilized. MacKenzie, A. P. (1966) Bull. Parenteral Drug Association 20, 101–129.

Sucrose was used to protect soybean phospholipid vesicles (liposomes) with membrane-associated cytochrome oxidase from damage during freeze-drying. Racker, E. (1972) J. Membrane Biol. 10, 221–235. The measure of intactness of the phospholipid vesicles was the ratio of uptake of oxygen with and without addition of a respiratory uncoupler. This ratio is called respiratory control (RC). After lyophilization and reconstitution with water, the respiratory control was completely abolished (RC=1.0). However, addition of sucrose to the vesicle suspension prior to lyophilization protected against damage. Increasing concentrations of sucrose up to 0.4M progressively increased respiratory control after lyophilization to a maximum of about RC=2.25. The author concluded that sucrose protects the structural organization of the phospholipids during freeze drying.

Other experiments involving liposomes made of egg phosphatidylcholine or 90% palmitoyloleoylphosphatidylcholine/10% phosphatidylserine have been done where a disaccharide such as trehalose, sucrose or maltose was present both inside and outside the liposome bilayer. Madden, T. D. et al. (1985) Biochim. Biophys. Acta 817, 67–74. Crowe, L. M. et. al. (1985) Arch. Biochem. Biophys. 242, 240–247. These lipids are called "fluid" because they exist in a liquid crystalline phase when hydrated at room temperature. Experiments done by Drs. John and Lois Crowe at the University of California at Davis indicate that these disaccharides alone function as cryoprotectants during lyophilization of large unilamellar liposomes composed of fluid phospholipids, and the studies conclude that 100% retention is achieved when a disaccharide is located inside as well as outside the liposome. The Crowes also found that the ratio of sugar to phospholipid is the key parameter' to successful lyophilization rather than the absolute concentration of sugar in solution. Putting the combination of at least one sugar and at least one protein, polypeptide and/or oligopeptide both inside and outside the liposome bilayer, claimed as one embodiment in the present invention, gives largely the same results. However, the Crowes found that only 42% of the active ingredient was retained if the disaccharide was added only to the outside. L. M. Crowe et al., Biophysical Journal, 47, 248a (1985).

Liposomes useful for stable encapsulation of pharmaceutical compounds to be carried to in vivo sites often require phospholipids of a less fluid nature such as dipalmitoylphosphatidylcholine (DPPC) or distearoylphosphatidylcholine (DSPC) and usually include cholesterol to strengthen the membrane bilayer. However, cholesterol in liposome bilayers can lead to more leakage and more fusion upon lyophilization and rehydration than for the same liposome composition without cholesterol. Crommelin, D. J. A. and vanBommel, E. M. G. (1984) Pharmaceutical Research 3, 159–163.

The aggregation of unilamellar liposomes comprised of these less fluid phospholipids with cholesterol useful in the present invention was not prevented by having a disaccharide located inside as well as outside the liposome as done by the Crowes. However, greater than 90% retention and almost no aggregation is shown by the present invention if a combination of at least one sugar and at least one protein, polypeptide and/or oligopeptide is added to the aqueous solution of phospholipids of a less fluid nature plus cholesterol prior to formation of the liposomes, such that the cryoprotectant solution is distributed both inside and outside the liposome bilayer.

The present invention is a composition to successfully make liposomes including those containing non-fluid phospholipids and cholesterol, such that up to 100% of the contents are retained and fusion and aggregation are largely inhibited. The composition uses, in one embodiment, a combination of at least one sugar and at least one protein, polypeptide, and/or oligopeptide in the aqueous solution used to make the liposomes.

It would therefore be advantageous to provide a commercially feasible process for the making of liposomes with or without drugs or other therapeutic agents, diagnostic agents, or other materials of biological interest with improved stability i.e. greater retention, little or no fusion and aggregation upon reconstitution. Moreover, if the cryoprotectants could be added to or included in the aqueous medium used to make the liposomes, rather than added later to already formed liposomes as described in Schneider et al., Process for the Dehydration of a Colloidal Dispersion of Liposomes, U.S. Pat. No. 4,229,360 (Oct. 21, 1980), it would simplify the manufacture of the dried liposome product. Furthermore, having the cryoprotectant solution distributed both inside and outside the liposome bilayer protects liposomes made of a broader range of phospholipids than could be shown by the Crowes.

SUMMARY OF THE INVENTION

The present invention relates to a commercially feasible process for making liposomes optionally containing sterols or other stabilizing molecules, particularly cholesterol, utilizing the combination of at least one sugar, preferably a disaccharide and at least one protein, polypeptide, and/or oligopeptide as cryoprotective agents in the aqueous medium in which the phospholipid(s) and optionally stabilizer mixture is hydrated prior to liposome formation. After lyophilization of liposomes made in this way, in excess of 90% intact liposomes are obtained upon reconstitution, and the reconstituted liposomes behave normally in in vivo applications and are essentially the same structure and size as their prelyophilized state, i.e. little or no fusion or aggregation has occurred. The liposome preparations that are stable during drying are claimed.

Figure 1A:
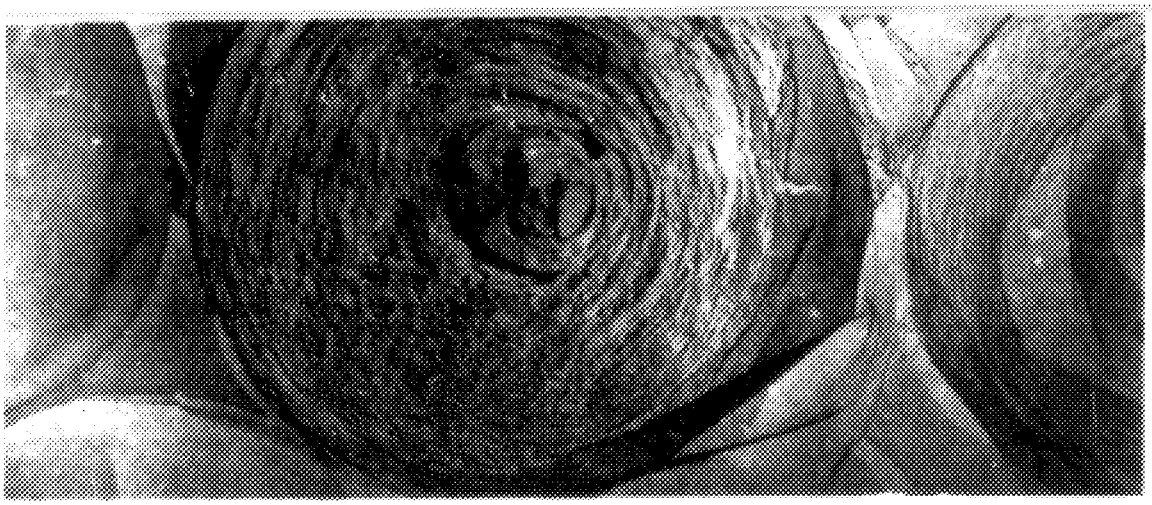
FIG. 1a is an electron micrograph taken by freeze-fracture electron microscopy, 41,000×magnification, showing rehydrated liposomes in PBS lyophilized without cryoprotection.
Figure 1B:
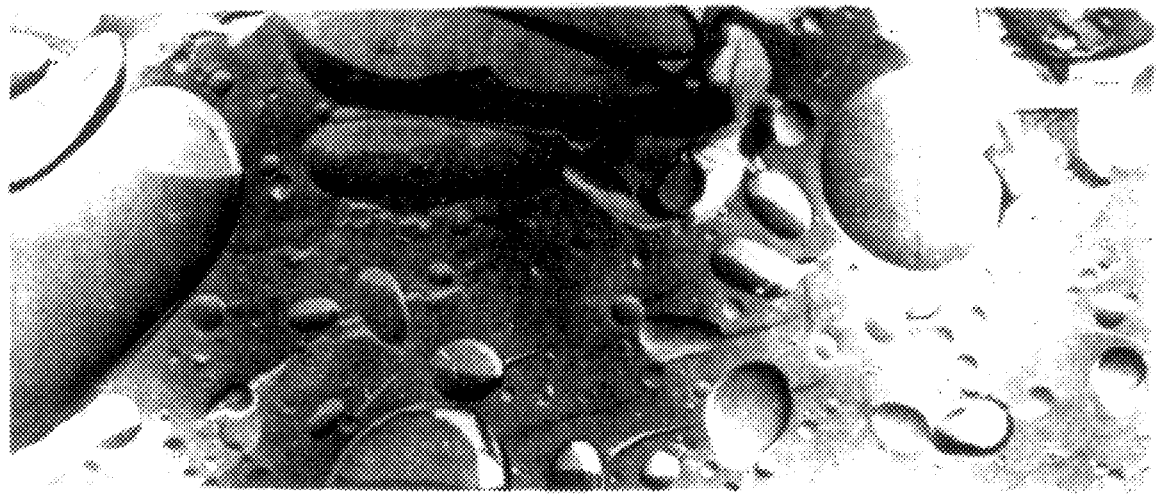
FIG. 1b is an electron micrograph taken by freeze-fracture electron microscopy, 21,000×magnification, showing rehydrated liposomes lyophilized with 9% w/v sucrose on the outside only.
Figure 1C:
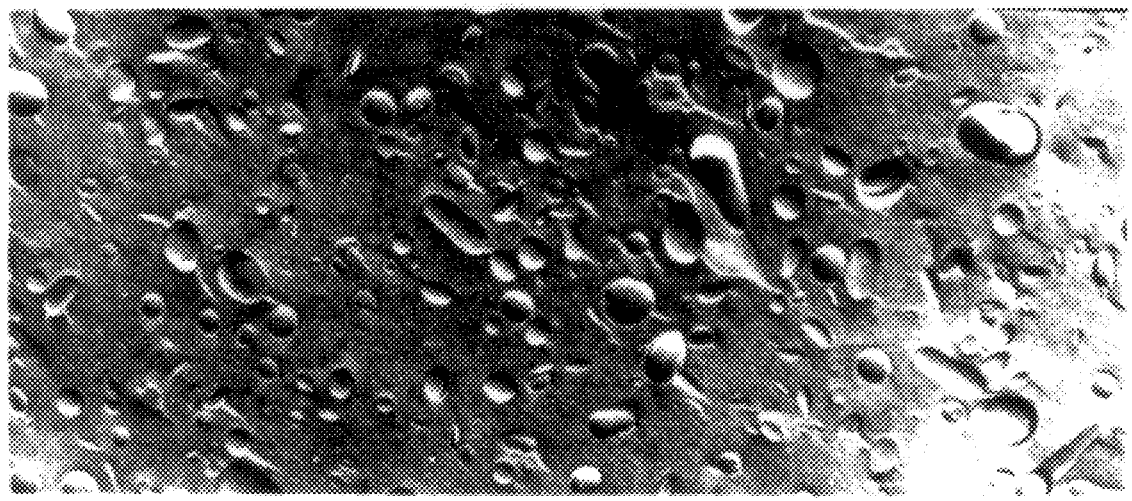
FIG. 1c is an electron micrograph taken by freeze fracture electron microscopy, 54,000×magnification showing rehydrated liposomes lyophilized with 9% w/v sucrose and 1.0 mg/ml gelatin on the outside only.

It has been observed that the cryoprotectant effect seen in FIG. 1c is equivalent to that seen with cryoprotectant inside and outside.

DETAILED DESCRIPTION OF THE INVENTION

"Micelles" refer to water-soluble particles which result from spontaneous aggregation of amphiphilic molecules. Amphiphilic molecules contain hydrophobic and hydrophilic portions. In this invention, preferred amphiphiles are biological lipids. Such micelles can be in the form of small spheres, ellipsoids or long cylinders, and can also consist of bilayers with two parallel layers of amphiphilic molecules.

Such bilayered micelles usually take the shape of unilamellar or multilamellar spherical shells with an internal aqueous compartment, and are also known as "liposomes."

Methods for forming these liposomes are, by now, well known in the art. Typically, they are prepared from phospholipids, for example, phosphatidylcholine by dispersion in aqueous solution and optionally, sonication or other cavitation methods and may include other materials such as neutral lipids, for example, cholesterol, and also surface modifiers such as positively or negatively charged compounds, saccharides, antibodies and other functional ligands which have groups that can anchor the molecule in the bilayer of the liposome.

Liposomes useful for in vivo pharmaceuticals delivery are not confined to formulations containing only phosphatidylcholine or other neutral phospholipids and stabilizing molecules such as cholesterol. Examples are formulations with phosphatidylserine, phosphatidylglycerol, phosphatidylethanolamine, cardiolipin and the like with or without sterols.

We have found that by incorporating certain phospholipid molecules, a liposome is obtained which is highly stable in vivo. It is known that phase transition points are a function of hydrocarbon chain length, C. Tanford, *The Hydrophobic Effect,* 2nd. Ed. (1980). Certain phospholipid molecules, for example those with hydrocarbon chains having at least 16 carbon atoms and no double bond are less fluid and exhibit phase transitions at relatively high temperatures (greater than 37° C.), and we have found that use of these phospholipids provides liposomes with improved stability in vivo. In some cases, due to availability and cost factors, it may be desirable to use phospholipids with shorter hydrocarbon chains, which may be added to the liposome formulations in small amounts such that a majority of the phospholipids present constitutes those molecules with saturated hydrocarbon chains of at least 16 carbon atoms to preserve the stability of the liposomes in serum.

The stability of phospholipid liposomes may be further enhanced by incorporating sterols particularly cholesterol or other stabilizing molecules. A stable liposome may be obtained by incorporating 25–50 mole % cholesterol into the liposomes. In liposomes made of distearoylphosphatidylcholine, cholesterol and the distearoylphosphatidylcholine are in a molar ratio ranging from about 1:1 to about 3:1, preferably 2:1.

Suitable for use as a cryoprotectant in the present invention is a combination of at least one sugar and at least one protein, polypeptide, and/or oligopeptide. The liposomes of the present invention which are stable during drying are made by adding the combination of at least one sugar and at least one protein, polypeptide and/or oligopeptide to the aqueous medium used to hydrate the phospholipid(s) and optionally preferably, cholesterol mixture prior to liposome formation. Alternatively, the combination can be added just to the aqueous medium external to the liposomes and the internal aqueous medium optionally containing at least one sugar or optionally at least one protein, polypeptide and/or oligopeptide. The sugar may be sucrose, lactose, trehalose, maltose, or glucose. The weight ratio of the sugar to phospholipid is from about 0.5:1 to about 10:1. In the case of lactose and sucrose, the weight ratio of sugar to phospholipid(s) is about 4:1. The concentration of sugar is from about 2.5% to about 15% (w/v). The protein may be, for example albumin and the polypeptide, gelatin or casein. The weight ratio relative to phospholipid of said protein, polypeptide, and/or oligopeptide is from about 1:100 to about 2:1. In the case of the protein albumin, the weight ratio of albumin to phospholipid is about 1:1. The weight ratio of casein and gelatin to phospholipid is about 1:10. It is believed that the action of gelatin, casein, and serum albumin as cryoprotectants relates, at least in part, to their polymeric nature. This is seen in Table IV where amino acids, the major constituents of polypeptides, do not provide cryoprotection for liposomes. The cryoprotection effect of polypeptides and proteins may arise from their ability to coat the surface of liposomes. In so doing they could provide a means of resisting the close juxtaposition of liposome surfaces that may occur during freezing and drying and thus prevent aggregation and fusion. For example casein is known to coat other surfaces that it comes in contact with. The area covered for one layer is 1.27 $M^2$ per mg casein. Encyclopedia of Polymer Science and Technology, Vol. 2 (1965) Interscience Publishers, pg. 861. A calculation of external surface areas of a solution of DSPC:cholesterol 2:1 liposomes 60 nm in average diameter and 25 mg/ml in lipid concentration gives about 5 $M^2$. A solution of 2.5 mg/ml kappa casein is sufficient for good cryoprotection. If all the protein formed a layer on the liposomes the protein molecules would cover 63.5% of the surface area, probably sufficient to prevent deleterious effect of lyophilization. Other mechanisms can be at work as well. It will be understood by those skilled in the art that various combinations of sugars and proteins, polypeptides and oligopeptides can be utilized within the confines of the present invention.

The liposomes of this invention include but are not limited to unilamellar phospholipid liposomes less than 2000 Å in diameter prepared by sonication as described by M. R. Mauk and R. C. Gamble, *Anal. Bioc.,* 94, p. 302–307 (1979), or by microemulsification using the procedures described in a co-pending application by R. Gamble filed Jan. 31, 1985, and assigned to the same assignee as this application, both incorporated by reference herein. However, it will be understood by those skilled in the art that other types of liposomes prepared by other means can be utilized within the confines of the present invention.

Any of a variety of compounds can be enclosed in the internal aqueous compartment of the liposomes. Illustrative therapeutic agents include antibiotics, metabolic regulators, immune modulators, chemotherapeutic drugs, toxin antidotes, etc. By the same token, the liposomes may be loaded with a diagnostic radionuclide and fluorescent materials or other materials that are detectable in in vitro and in vivo applications.

In the preferred embodiment of this invention, the liposomes are preferably unilamellar phospholipid lipsomes containing cholesterol which are formed in the presence of a combination of at least one sugar and at least one protein, polypeptide and/or oligopeptide which have been added to the aqueous medium used to hydrate the phospholipid(s) and cholesterol mixture.

In an alternative embodiment of the invention, the combination of at least one sugar and at least one protein, polypeptide and/or oligopeptide is added to the liposomes after formation. The liposomes' internal aqueous medium may contain at least one sugar or at least one protein, polypeptide and/or oligopeptide.

The present invention is most advantageous as it stabilizes the liposome against damage during the drying process and subsequent reconstitution. By "stabilizes", it is meant that average size and size distribution are not affected, i.e., that little or no fusion or aggregation is observed upon reconstitution, that the liposome bilayer integrity is maintained, and that there is no sacrifice of the utility of the liposome caused by leakage.

The example which follows illustrates the preparation, characterization and in vivo application in an animal model of a lyophilized liposome product. Results from a freeze-thaw liposome product are shown as a means of comparison only.

The following example is intended to illustrate the invention, and is not intended to limit the scope thereof.

General Liposome Preparation

Small unilamellar vesicles (SUV) (liposomes) optionally with trace amounts of the ionophore A23187 were prepared from distearoyl phosphatidylcholine (DSPC) and cholesterol (Ch)(2:1 molar ratio) according to previous methods. Mauk and Gamble, *Anal. Bioc.*, 94, 302–307 (1979), incorporated by reference herein. Briefly, a chloroform solution of 40–100 mg lipid (DSPC and Ch) was evaporated to dryness under nitrogen ($N_2$) and further dried under vacuum overnight. The tube was filled with a volume of buffer or cryoprotectant solution optionally containing 1 mM nitrilotriacetic acid (NTA) or 100 mM 6-carboxyfluorescein and sonicated under $N_2$ at 60°–70° C. for 5 to 15 minutes with an MSE brand probe sonicator equipped with a titanium microtip. Sonication or microemulsification yielded the small unilamellar liposomes used throughout these experiments.

After sonication unencapsulated outer solution was exchanged for PBS or cryoprotectant solution on a Sephadex G-50-80 column with vacuum elution. Final lipid concentration was in the range of 20–30 mg/ml.

Screening of Excipients for Cryoprotection

Testing of a particular compound or compounds as potential cryoprotectants consisted of four steps: Candidate cryoprotectants in varying amounts were added to a volume of the liposome preparation. The next step was a qualitative visual check of the sample after the addition of the potential cryoprotectant to see if there were any immediate effects. If the sample appeared to be stable, i.e., appeared not to aggregate after addition of the agents, then it would be subjected to freezing and thawing and/or lyophilization. For freeze-thaw, samples were frozen at −18 degrees °C., and thawed at room temperature (21 degrees °C.). For lyophilization, the samples were frozen at −18° C. and then placed under vacuum (Virtis Freeze Dryer Model G) for at least 24 hours.

Reconstitution

Lyophilized liposome samples were reconstituted by adding distilled water and gently agitating the vial by hand.

Visual Check

The reconstituted liposome preparations were first visually checked for any large particles, aggregates, or other changes in the solution which might indicate instability. The liposomes were then centrifuged for 3 minutes in an Eppendorf Model 5414 Centrifuge at 15600 g. The centrifuge tube was checked to see if large pellets formed at the bottom of the tube, a finding which disqualified a sample from further consideration. Results are shown in Table I.

Characterization of Liposome Integrity

Fluorescent Dye Release

Liposome bilayer integrity was tested using fluorescent dye release data obtained by measuring the release of encapsulated 100 mM 6-carboxyfluorescein from lyophilized liposomes which had been reconstituted. The sample fluorescence was measured with a HPLC fluorescence detector. A portion of the sample, held back from lyophilization, was measured to provide a "background" fluorescence value. The % release values were calculated by subtracting the background fluorescence from the sample fluorescence and dividing by the total fluorescence minus the background fluorescence of the lysed liposomes (Triton X-100, 0.4% was used to lyse the liposomes). Percent retention was calculated as 100% minus % released. Results are shown in Table II.

Particle Size Measurements

Lactose and Polypeptides

Liposomes as previously prepared were suspended in lactose (90 mg/ml) with 5 mM phosphate at pH 7.4. Lactose was present on the outside of the liposomes only. PBS was in the inside of the liposomes.

The stock of SUV solution was divided into 2 ml volumes in 10 ml septum bottles, and measured portions of bovine milk kappa casein, bovine milk casein-o-glycopeptide, fish skin gelatin and bovine skin gelatin (60 Bloom), all from Sigma Chemical Co. and used without further purification were added. The samples were loaded into a freeze dryer with temperature controlled shelves, frozen and dried by vacuum over a 3 day period with programmed shelf temperature.

After freeze-drying, the samples were reconstituted with a volume of distilled water equal to the starting volume. Mean vesicle diameters were determined by dynamic light scattering using a Nicomp model 270 instrument in the volume-weighted Gaussian mode. Samples were tested both before and after centrifuging at 15,600 g for 10 min. to remove aggregates and precipitated material, present in some reconstituted samples. Results are shown in Table III.

Amino Acids

Amino acids were also tested for their cryoprotectant ability. Weighed samples of 10 mg/ml of amino acids (Sigma Chemical Co.) were added to liposomes in which 9% sucrose was contained in the external aqueous medium. The samples were frozen and lyophilized using a shelf dryer. Following lyophilization the samples were reconstituted with deionized water, gently agitated and warmed to about 30° C. and examined for precipitate indicating irreversible aggregation, fusion and/or breakage. While the amount of precipitate varied among the samples, in all cases there was substantial insoluble material indicating the failure of amino acids to protect against lyophilization damage. Average size and size distribution were then measured for the supernatants. Results are shown in Table IV.

Freeze-Fracture Electron Micrograph Evidence for Protective Effects on Liposomes after Lyophilization and Rehydration Samples of DSPC:cholesterol (2:1) SUV were prepared in phosphate buffered saline (PBS) as described. Portions were exchanged for sucrose (9% w/v) (90 mg/ml) with 5 mM phosphate buffer pH 7.4, on the outside of the liposomes, using Sephadex G-50 column chromatography. Weighed aliquots of 60 Bloom bovine skin gelatin (Sigma Chemical Co.) (1.0 mg/ml) were added to some samples and dissolved. Two ml volumes of test liposome solutions were frozen and lyophilized in a freeze dryer with shelf temperature control.

Dried samples were prepared for freeze-fracture electron microscopy by suspending them in paraffin oil to hold the granular material together. The samples were rehydrated in 50% glycerol/water before freeze-fracturing. The samples were then rapidly frozen and cleaved with a Balzers BAF 400D freeze-fracture apparatus with Pt shadowing at a 45° angle. Replicas were examined in a Phillips 410 electron microscope. Results are shown in FIGS. 1a–1c.

In the presence of sucrose and 1.0 mg/ml gelatin the liposomes are intact after rehydration (FIG. 1c), not fused or aggregated, and of a size similar to that measured in solution before lyophilization. With sucrose outside only but no polypeptide in the medium the dried sample after rehydration (FIG. 1b) shows many large unilamellar structures representing fused liposomes (21,000 magnification). Note that the magnification of 1b is approximately one-half that of 1c. Without any cryoprotectants being added, the liposomes completely collapse after drying and rehydration and form multilamellar vesicles whose contents are largely lost and whose large size prevents proper biodistribution (FIG. 1a).

Biological Efficacy of Lyophilized and Reconstituted Liposomes In-111 Loading Procedure Loading of In-111 into preformed liposomes containing NTA was facilitated by the presence of the ionophore A23187 in the lipid bilayer. In-111 was loaded into liposomes at 80° C. as described by Mauk and Gamble, *Anal. Bioc.*, 94, 302–307 (1979) except for those with bovine serum albumin where a temperature of 65° C. was used. Incubations were terminated by the addition of 0.1 ml of 10 mM EDTA in phosphate buffered 0.9% sodium cholride, pH 7.4 (PBS), and unencapsulated In-111 was separated from the loaded liposomes by chromatography on Sephadex G-50. Over 90% of the added In-111 could be incorporated into intact preformed liposomes by this technique.

Loading efficiencies were checked by adding a portion of loaded liposome solution to a centrifuge tube containing Chelex-100 prior to addition of EDTA. After centrifuging the tube, the supernatant was measured for $^{111}$In in a gamma counter to determine the percent of radioactivity remaining with the liposomes. Results are shown in Table V.

EMT6 TUMOR MODEL

Biodistribution studies were carried out by tail vein injection of 200 μl of 10 mg/ml lipid concentration $^{111}$In loaded liposome samples. BALB/c female mice (19±1 gm) were used with eight day old EMT6 tumors implanted in the flank. Five mice were injected per sample. After 24 hours the mice were euthanized and tissue biodistribution of $^{111}$In was performed. Control animals were injected with liposomes which had not been lyophilized but which had the excipients added and/or which contained only PBS. The liver, tumor, spleen, and blood were collected and samples were counted using a Beckmann 5500 gamma counter. Results are also shown in Table V.

Comparison of Size Retention and Precipitation for Liposomes with Cryoprotectants Placed Inside Only, Outside Only, or Both Inside and Outside The effects of placing cryoprotectants inside liposomes only or outside only or both inside and outside were tested. Samples of DSPC/cholesterol liposomes were prepared in 9% (w/v) lactose (Lac) or 9% (w/v) lactose plus 2.5 mg/ml gelatin (60 Bloom) (Lac-Gel). A separate sample of DSPC/cholesterol liposomes encapsulating PBS was also used. These preparations were exchanged for PBS, Lac or Lac-Gel as needed with gel chromatography to generate all permutations of cryoprotectants or buffer inside and outside the liposomes.

Samples of each preparation were measured for the mean diameter by light scattering, then aliquots were frozen and lyophilized. The dry samples were then reconstituted with distilled water. Portions of the total reconstituted samples were centrifuged at 15600 G for 10 minutes and the supernatant was measured for the mean diameter. Another aliquot of the total solution was taken for measurement of cholesterol concentration by high performance liquid chromatography and a similar aliquot of the supernatant after centrifuging was also measured for cholesterol concentration. Analysis of these concentrations gave the % of material that was precipitated after lyophilization. Results are shown in Table VI.

RESULTS

Listed in Table I are the results of the qualitative tests of the potential cryoprotectants tried. Pluses indicate a positive result for that particular test. Minuses indicate an unsatisfactory result due to precipitation or failure to resuspend completely. If a sample received a minus upon addition of the agent(s) or during freeze/thaw then no further experiments were attempted with that agent. The only cryoprotectants that were able to pass all three tests were the combination of a sugar and a protein, polypeptide and/or oligopeptide.

Table II shows the % retention of 6-carboxyfluorescein for liposomes in the presence of different concentrations of bovine serum albumin (BSA), serum and lactose. Low retention values indicate liposome breakage. Lyophilization causes liposomes to break and leak (less than 90% retention) unless both sugar and a protein, polypeptide, and/or oligopeptide are present.

Tables III and IV show changes in particle size with different concentrations of protein or amino acids plus disaccharide after lyophilization. Increased size after reconstitution indicates aggregated and/or fused liposomes. The particle sizing data indicate that at least 25 mg/ml BSA (bovine serum albumin)/9% disaccharide is necessary for cryoprotection while only 2.5 mg/ml gelatin/9% disaccharide works to preserve liposomes. Without lyophilization a lactose solution of SUV has a mean diameter of about 50 nm. The same sample after lyophilization and reconstitution produces a precipitate, has a mean diameter of 104.9 nm before centrifugation and 88.3 nm for the supernatant after centrifugation. The presence of precipitate and large change in average size are unacceptable for an injectable liposome preparation.

At 2.5 mg/ml, bovine gelatin and bovine milk kappa-casein produced no visible precipitate, mean diameters of 57–58 nm before centrifugation, and diameters of 53–54 nm after centrifugation. Fish skin gelatin at 1.0 mg/ml was almost as effective with diameters of 57.5 and 56.2 nm pre- and post-centrifugation, respectively. 2.5 mg/ml of fish skin gelatin produced an anomalous result with a larger mean diameter after centrifugation. Casein-o-glycopeptide failed to protect the liposomes from precipitation after lyophilization and reconstitution.

Table IV shows that amino acids, even though they represent the major constituents of kappa-casein, for example, do not provide the liposome cryoprotection of the same weight concentration or less of the polypeptide.

Table V lists biodistribution results for several different samples. Performance in the loading and biodistribution tests is critical to assessment of liposome viability. Low values (<75%) in loading imply breakage of liposomes so as to provide NTA in the exterior solution which competes with NTA inside liposomes for $^{111}$In. The % injected dose recovered usually measures liposome "toughness" in circulation.

Low values here compared to control level might suggest that a sample suffered partial damage to the liposome bilayer. Lyophilized BSA/sugar liposomes show lower percent injected dose recoveries while the gelatin/sugar lyophilized liposomes biodistribute as well as an unlyophilized liposome preparation.

The tumor-to-liver ratio of $^{111}$In uptake is a traditional key test of liposome performance. Values above 1.2 are found for a normal unlyophilized liposome preparation. Lyophilized liposome preparations containing gelatin and lactose, tested within a few hours of reconstitution, show good tumor to liver ratios, as well as normal values for the other parameters (Table V).

The results show that lyophilization of DSPC:cholesterol liposomes was most successful when both a sugar and at least one protein, polypeptide and/or oligopeptide were present. Lactose and sucrose worked equally well, and other disaccharides, e.g. trehalose and maltose will also provide the advantage of the invention. Gelatin and casein were found to be the best polypeptides for lyophilization. A 2.5 mg/ml gelatin or casein concentration is all that was needed in combination with 9% sugar to get preservation of liposomes.

Table VI shows that while PBS buffer outside liposomes produces more than 84% precipitation in all cases, inclusion of 9% (w/v) lactose in the outside solution prevented precipitation in two of three samples. However, lactose only outside was insufficient to prevent aggregation as evidenced by an increase of more than 50% in the mean liposome diameter after reconstitution, for all samples.

With Lac-Gel outside there was less than 10% precipitation in all cases and less than a 23% increase in mean diameter. With Lac-Gel both inside and outside, the size of the liposomes remained virtually the same after reconstitution.

TABLE I

TEST RESULTS OF POTENTIAL CRYOPROTECTANTS
25 mg/ml LIPID CONCENTRATION (DSPC:cholesterol, 2:1)

| SAMPLE (conc or range) | AFTER ADDITION OF AGENT[a] | After Freeze/ Thaw | After Lyophilization and Reconstitution |
|---|---|---|---|
| 5 mM Phosphate Buffered Saline | + | −[b] | |
| 25 mM Ca$^{+2}$ | + | − | |
| Low pH 4.0 | + | − | |
| High pH 10.0 | + | − | |
| 5 mM Tris buffered saline (0.9%) | + | − | |
| 5 mM Tris buffered dextrose (5%) | + | − | |
| 5 mM Tris buffered lactose (9%) | + | − | |
| 5% Dextrose (5 mM Pi) | + | − | |
| 9% Lactose (5 mM Pi) | + | + | − |
| 9% Sucrose (5 mM Pi) | + | + | − |
| 10% N-Methyl-Pyrrolidone | + | − | |
| Gycerol (10 mg/ml) | + | + | − |
| Glycerol (10 mg/ml)/9% lactose | + | + | − |
| PEG[c] 400 (10 mg/ml) | + | − | |
| PEG 1450 (10 mg/ml) | − | | |
| PEG 3350 (10 mg/ml) | − | | |
| PEG 4000 (10 mg/ml) | − | | |
| PEG 8000 (10 mg/ml) | − | | |
| Dextran 40,000 (10 mg/ml) | − | | |
| Dextran 500,000 (10 mg/ml) | − | | |
| Polyvinylpyrrolidone (10 mg/ml) | + | + | − |
| Ficoll (10 mg/ml) | + | + | − |
| Hydroxyethylcellulose (10 mg/ml) | − | | |
| Serum[d] (20 mg/ml) | + | + | − |
| Bovine Serum Albumin (25 mg/ml) | + | + | − |
| Gelatin[e] (10 mg/ml) | + | + | − |
| 9% Lactose/20% Serum | + | + | + |
| 9% Lactose/Albumin (25 mg/ml) | + | + | + |
| 9% Lactose/gelatin (5.0 mg/ml) | + | + | + |
| 9% Sucrose/gelatin (5.0 mg/ml) | + | + | + |

[a]+: Retains original qualitative solution characteristics.
−: Fails to stabilize liposomes as measured by different analytical methods.
[b]If a cryoprotectant received a minus at any stage of testing then no further tests were attempted using that cryoprotectant.
[c]Polyethylene glycol
[d]Bovine fetal serum
[e]"Knox" gelatin

TABLE II

STABILITY OF LIPOSOMES TO LYOPHILIZATION
ASSAYED BY CARBOXYFLUORESCEIN RELEASE

| SAMPLE | % RETENTION OF CONTENTS AFTER LYOPHILIZATION AND RECONSTITUTION |
|---|---|
| LIPOSOMES IN 9% LACTOSE (Outside only) 25 MG/ML LIPID CONCENTRATION | |
| CONTROL (9% lactose only) | 72.5 |
| 9% lactose and 20% SERUM | 98.8 |
| 9% lactose and 25 mg/ml BSA | 97.8 |
| 9% lactose and 10 mg/ml BSA | 97.0 |
| 9% lactose and 5 mg/ml BSA | 95.8 |
| LIPOSOMES IN PBS (no disaccharide) 25 MG/ML LIPID CONCENTRATION | |
| CONTROL (PBS only) | 79[a] |
| 20% SERUM | 82 |
| 25 mg/ml BSA | 18 |
| 20 mg/ml BSA | 0 |
| 10 mg/ml BSA | 44 |
| 5 mg/ml BSA | 79 |

[a]Highly variable from experiment to experiment.

TABLE III

LASER PARTICLE SIZING DATA FOR LYOPHILIZED
LIPOSOMES AFTER RECONSTITUTION WITH DISTILLED
WATER 25 mg/ml LIPID CONCENTRATION

| | UNCENTRIFUGED | CENTRIFUGED |
|---|---|---|
| Control 9% (Lactose outside liposome (not lyophilized) | 48.0 | 49.9 |
| 9% Lactose | 104.9 | 88.3 |
| 9% Lactose and 2.5 mg/ml gelatin (60 Bloom) | 58.1 | 53.0 |
| 9% Lactose and 2.5 mg/ml k-casein | 57.0 | 53.8 |
| 9% Lactose and 2.5 mg/ml fish skin gelatin | 49.7 | 58.9 |
| 9% Lactose and 2.5 mg/ml casein-o-glycopeptide | 284.1 | 96.1 |
| 9% Lactose and 1.0 mg/ml gelatin (60 Bloom) | 72.2 | 64.9 |
| 9% Lactose and 1.0 mg/ml k-casein | 65.4 | 67.1 |

TABLE III-continued

LASER PARTICLE SIZING DATA FOR LYOPHILIZED LIPOSOMES AFTER RECONSTITUTION WITH DISTILLED WATER 25 mg/ml LIPID CONCENTRATION

|  | UNCENTRIFUGED | CENTRIFUGED |
|---|---|---|
| 9% Lactose and 1.0 mg/ml fish gelatin | 57.5 | 56.2 |
| 9% Lactose and 1.0 mg/ml casein-o-glycopeptide | 86.2 | 82.5 |

TABLE IV

| Amino Acid | Pellet Size[1] | Average Size[2] nm |
|---|---|---|
| proline | 6 | 78.5 |
| glycine | 7–9 | 144 |
| alanine | 3–5 | 70.9 |
| glutamic acid | 7–9 | 53.3 |
| isoleucine | 8 | 73.8 |
| methionine | 7 | |
| valine | 6 | 76.1 |
| serine | 7 | 74.5 |
| leucine | 7 | 56.9 |

[1]Graded as 0 - no pellet to 9 heavy pellet after 10 minutes centrifuging at 15,600 g.
[2]Measured on supernatant after centrifugation.

TABLE V

BIODISTRIBUTION DATA

| EXPT. | SAMPLE | LOADING EFFIC. | TUMOR/ LIVER RATIO | % ID RECOV. |
|---|---|---|---|---|
| A. | 1. Control 5/8/86[a] | 109% | 1.38 | 35.4 |
|  | 2. Lyophilized 9% Lactose/5 mg/ml gelatin | 98% | 1.24 | 31.0 |
|  | 3. Not lyophilized 9% Lactose/5 mg/ml gelatin | 101% | 1.30 | 35.7 |
| B. | 1. Control 5/15/86 | 98% | 1.42 | 36.2 |
|  | 2. Lyophilized 9% Lactose/2.5 mg/ml gelatin | 96% | 1.32 | 35.8 |
|  | 3. Not Lyophilized 9% Lactose/2.5 mg/ml gelatin | 89% | 1.18 | 35.3 |
| C. | 1. Control 3/27/86 | 82% | 1.39 | 34.8 |
|  | 2. Lyophilized 9% Lactose/5 mg/ml BSA | 86% | 1.12 | 30.1 |

[a]Control samples are unlyophilized liposomes without addition of cryoprotectants.

TABLE VI

MEAN DIAMETER AND PRECIPITATION OF LIPOSOMES AFTER LYOPHILIZATION AND RECONSTITUTION. DEPENDENCE ON PRESENCE OF SUGAR AND POLYPEPTIDE INSIDE LIPOSOMES

| Sample[a] | Mean Size (nm)[b] prelyo | postlyo | % Precipitation[c] |
|---|---|---|---|
| PBS in PBS out | 68 | d | 94.5 |
| PBS in Lac out | 68 | 132 | 0 |
| PBS in Lac-Gel out | 68 | 83 | 0 |
| Lac in PBS out | 59 | d | 89.9 |
| Lac in Lac out | 59 | 106 | 52.5 |
| Lac in Lac-Gel out | 59 | 48 | 9.1 |
| Lac-Gel in PBS out | 59 | d | 84.1 |
| Lac-Gel in Lac out | 59 | 89 | 0 |
| Lac-Gel in Lac-Gel out | 59 | 60 | 7.6 |

[a]Liposomes were composed of DSPC and cholesterol in a 2:1 molar ratio. Final concentration was 25 mg/ml total lipid (20 mg DSPC and 5 mg cholesterol/ml). Lac was 9% (w/v) lactose; Lac-Gel is 9% lactose (w/v) plus 2.5 mg/ml gelatin, 60 bloom.
[b]Laser light scattering measurement. The volume weighted Gaussian mean diameter is reported.
[c]Precipitation after reconstitution was measured by assaying for liposomal cholesterol on the total sample and on the supernatant after centrifuging at 15600 G for 10 minutes. The % Precipitation value was determined from the equation $$100 - \left[ \frac{(Chol)_{total} - (Chol)_{super}}{(Chol)_{total}} \right] \times 100 = \% \text{ Precipitation}$$

Negative numbers were rounded to 0.
[d]Due to precipitation of all or a large fraction of the sample the light scattering data were unobtainable.

We claim:

1. A protectant preparation for stabilizing liposomes during lyophilization, comprising phospholipid containing liposomes, having an internal aqueous medium and dispersed in an external aqueous medium while the liposomes are subjected to drying, wherein the external aqueous medium comprises at least one sugar selected from the group consisting of sucrose, trehalose, lactose, maltose and glucose and at least one protein selected from the group consisting of gelatin and casein; wherein said at least one sugar is present in said protectant preparation in a weight ratio to phospholipid of from about 0.5:1 to about 10:1 and the protein is present in said protectant preparation in a weight ratio to phospholipid of from about 1:100 to about 2:1.

2. The protectant preparation of claim 1 in which the internal aqueous medium of the liposomes comprises said at least one sugar.

3. The protectant preparation of claim 1 in which the internal aqueous medium of the liposomes comprises said at least one protein.

4. The protectant preparation of claims 1, 2, or 3 in which the at least one protein is gelatin.

5. The protectant preparation of claims 1, 2, or 3 in which the liposomes further include cholesterol.

6. The protectant preparation of claim 4 in which the liposomes further include cholesterol.

7. A method comprising preparing phospholipid containing liposomes having an internal aqueous medium and dispersed in an external aqueous medium wherein the external aqueous medium comprises at least one sugar selected from the group consisting of sucrose, trehalose, lactose, maltose and glucose and at least one protein selected from the group consisting of gelatin and casein; wherein said at least one sugar is present in a weight ratio to phospholipid of from about 0.5:1 to about 10:1 and the protein is present in a weight ratio to phospholipid of from about 1:100 to about 2:1; and then lyophilizing the liposomes.

8. The method of claim 7 in which the internal aqueous medium of the liposomes comprises said at least one sugar.

9. The method of claim 7 in which the internal aqueous medium of the liposomes comprises said at least one protein.

10. The method of claims 7, 8 or 9 in which the at least one protein is gelatin.

11. The method of claims 7, 8, or 9 in which the liposomes further include cholesterol.

12. The method of claim 10 in which the liposomes further include cholesterol.

* * * * *